United States Patent [19]

Böhme et al.

[11] Patent Number: 4,623,792
[45] Date of Patent: Nov. 18, 1986

[54] CORE LOGGING

[75] Inventors: Rolf C. Böhme, Midrand; Max M. Lazerson, Johannesburg, both of South Africa

[73] Assignee: General Mining Union Corporation Limited, Johannesburg, South Africa

[21] Appl. No.: 714,245

[22] Filed: Mar. 21, 1985

[30] Foreign Application Priority Data

Mar. 23, 1984 [ZA] South Africa ................. 84/2155

[51] Int. Cl.⁴ ............................................. G01N 37/00
[52] U.S. Cl. ................................. 250/255; 250/359.1; 250/360.1
[58] Field of Search .................. 73/153; 250/253, 254, 250/255, 360.1, 359.1, 358.1, 393, 363 SB, 363 R, 361 R, 363 SA

[56] References Cited

U.S. PATENT DOCUMENTS

| 3,025,398 | 3/1962 | Dameron | 250/255 |
| 3,373,440 | 3/1968 | Jenkins et al. | 346/107 R |
| 4,149,804 | 4/1979 | Chew, III | 356/416 |
| 4,531,058 | 7/1985 | Burnham et al. | 250/363 S |
| 4,542,648 | 9/1985 | Vinegar et al. | 73/153 |

Primary Examiner—Janice A. Howell
Assistant Examiner—Constantine Hannaher

[57] ABSTRACT

In the logging of a grade characteristic of a borehole core, the core is placed in a trough which is caused to move, in step fashion, through an annular detector. For each step the detector measures a characteristic of a notional segment of the core. The measures are corrected to compensate for contributions due to adjacent notional segments. The correction factor is derived by passing a core segment of known characteristics through the detector under controlled conditions.

2 Claims, 8 Drawing Figures

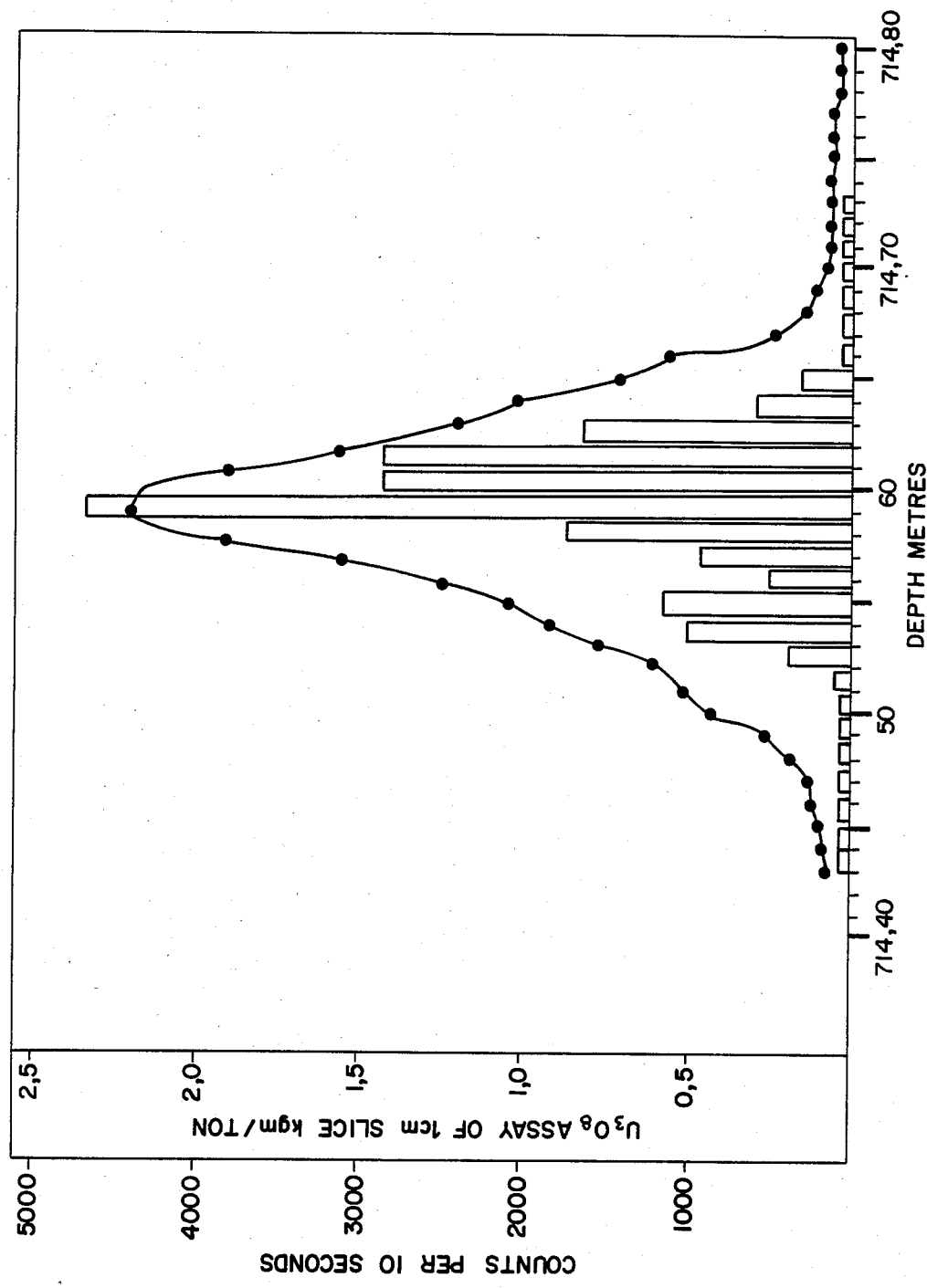

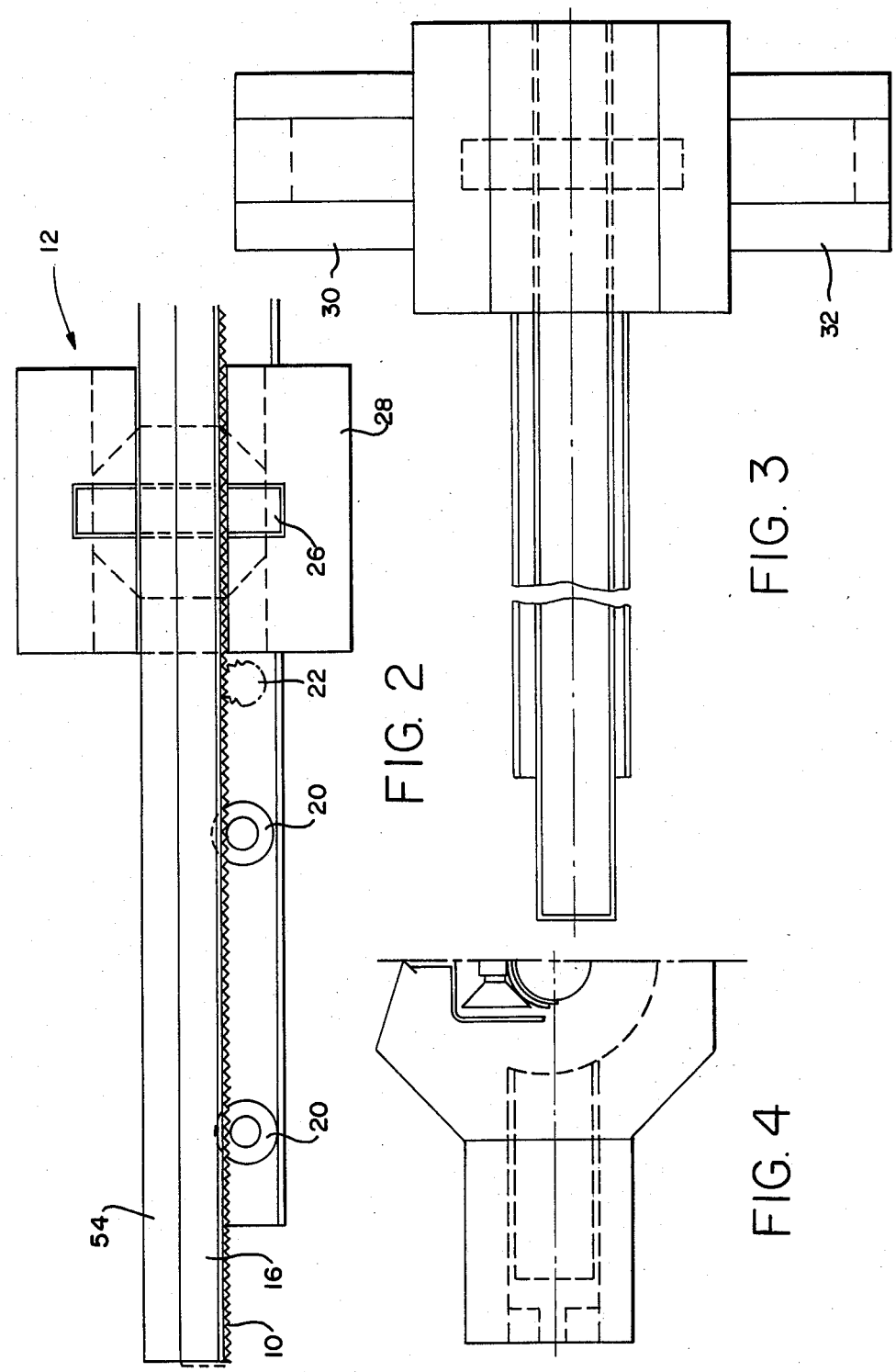

CORE LOGGING

BACKGROUND OF THE INVENTION

This invention is related to the logging of data obtained from cores produced by the drilling of core boreholes. The principles of the invention are particularly applicable to the evaluation of radiometric data but are equally applicable to the measurement of emissivity of practically any nature, especially under circumstances where the source of the emission is not easily localized.

In the drilling of core boreholes for exploratory and survey work in uranium mining, the resulting cores are usually evaluated visually and the visual geological and mineralogical features of sections of apparent principal interest are logged in detail. At least some of the sections of the core are split longitudinally and assayed for minerals of interest. In this process the split section of core which is used is destroyed.

The core is often assayed in sections which are approximately 10 cm long and the results are reported in terms of the milling width. The milling width is generally of the order of from 1 m to 1,5 m. The assay thus gives the average mineral content over the milling width, this data being required for an economic evaluation of the ore body, but it gives little information on the detailed grade or value distribution of the uranium over the length of the core, for example whether the reef is wide and of a low grade or narrow and of a relatively higher grade. This information may in some cases be indicated by the visual log of the core but this can be deceptive.

In many instances a detailed knowledge of the value or grade distribution over the milling width is not required for certain decisions based on economic considerations of a particular deposit but such knowledge can be of considerable value for optimum metallurgical processing, and for geologists and sedimentologists. Detailed information on the grade distribution over the milling or mining width does, however, become essential in the evaluation for any ore sorting or ore upgrading operation whether this be based on radiometric or heavy media techniques.

For example in the case of radiometric sorting of uranium bearing ores a reef which is 1 m wide and which has an average uranium content of 0.1 kg uranium per ton over the 1 m reef and milling width would not be sortable while a reef which is 10 cm wide with a uranium grade of 1 kg uranium per ton over the 10 cm reef width, but also having an average grade over the 1 m milling width of 0.1 kg uranium per ton would be eminently sortable, with over 80% of the mined ore being discarded or rejected in the sorting operation and with about 98% of the total uranium content being recovered.

SUMMARY OF THE INVENTION

It is an object of the present invention to provide an improved method of logging a grade distribution of a borehole core. The expression "grade distribution" is intended to include an indication of the quantity of a given type of material which is responsible for emission of a particular nature from the core. Generally the source of the emission is not readily localized. For example a core possessing radioactive material displays this characteristic.

The invention provides a method of logging a grade distribution of a borehole core which includes the steps of notionally dividing the core into a plurality of contiguous segments, obtaining a measure of a characteristic of each segment, and recording the measure for each segment.

The segments may extend in the axial or longitudinal direction of the core.

The characteristic may be a surface characteristic e.g. contrasting colour of the core within each segment, or the like. This may be produced under irradiation e.g. by means of a laser or other energy source. It is envisaged though that the method of the invention will generally be employed under conditions in which the characteristic will result in emission at a particular wavelength or wavelengths and thus the measure may be of the emissivity of each segment. In these circumstances the invention preferably includes the feature of correcting the emissivity measure of each segment to compensate for contributions to the measure due at least of adjacent segments, and recording the corrected emissivity measure for each segment.

The method may be preceeded by the initial step of deriving a correction factor which is used in the compensating process. The correction factor may be derived from measurements taken of the emission of a segment of known characteristics positioned in an otherwise barren core.

The segments may be of any suitable thickness but preferably are all of the same thickness which is selected according to requirement and constraints imposed by the apparatus used for carrying out the method of the invention.

An emissivity measure may be obtained for each segment over a predetermined period of time which may be varied according to requirement.

The method of the invention may be implemented by causing relative stepped movement of the core and suitable measuring apparatus, each step of movement corresponding to the thickness of one segment, maintaining the core stationary relatively to the apparatus for a predetermined measuring period, making a measure of the characteristic of a predetermined segment, recording the measurement of the characteristic, and repeating the process as to obtain a measurement of the characteristic for each of the segments in succession.

The core may be maintained stationary relatively to the measuring apparatus at least while the emissivity measurements are being recorded.

The invention also extends to apparatus for logging a grade distribution of a borehole core which includes means for obtaining a measure of a characteristic of each of a plurality of notional segments of the core and means for recording the measure for each segment.

The characteristic may result in emission e.g. at a particular wavelength from the segment and the emissivity may therefore be measured. The apparatus may include means for correcting the emissivity measurements of each segment to compensate for contributions to the measure which are due at least to adjacent segments. The corrected emissivity measure for each segment may be recorded.

Means may be provided for causing relative movement of the core and the measuring means. The relative movement of the core and measuring means may be stepped, with movement taking place in the longitudinal direction of the core, and with the length of each step of movement corresponding to the thickness of a notional segment in the longitudinal direction of the core.

Thus according to one embodiment of the invention the apparatus may include means for receiving the core, emissivity detection means, and means for causing step movement of the core receiving means together with the core relatively to the emissivity detection means.

The emissivity detection means may include annular detection means through which the core is passed.

Means may be provided for controlling the length of each step of movement, the speed of movement, and for maintaining the core stationary relatively to the emissivity detection means for a predetermined period. The said predetermined period may be varied according to requirement and may be equal to, but preferably is greater than, the period for which the emissivity of each segment is measured. During the remaining interval in which the core is held relatively stationary data on the emissivity measurement may be transferred to the recording means.

The recording means may take on any suitable form but preferably includes a computer.

As indicated the invention finds particular application in radiometric core logging systems. In this particular case the emissivity detection means may include an annular thallium activated sodium iodide scintillation crystal.

The computer program may include a correction factor based on emissivity measurements made of a core segment of known material content located in an otherwise barren core.

If the emissivity which is to be detected is not natural then it may be stimulated and for this purpose the apparatus described may include means for irradiating the core with suitable radiation. The intensity nature and period of irradiation may be varied according to requirements. For example use may be made of neutron activation, X-rays, lasers, ultraviolet radiation, or the like, depending on the core material and characteristics which are being sought.

BRIEF DESCRIPTION OF THE DRAWINGS

The invention is further described by way of example with reference to the accompanying drawings in which:

FIG. 1 illustrates (a) in a continuous curve a radiometric scan of a core taken in predetermined steps, and (b) a histogram generated by assaying core segments cut from the core used to generate the continuous curve referred to, FIG. 2 is a side view of apparatus according to the invention, FIG. 3 is a plan view of the apparatus of FIG. 2, FIG. 4 is an end view of the apparatus of FIG. 2, (the apparatus is symmetrical about a central axis and therefore only half of the apparatus is shown), FIG. 5 schematically illustrates, in block diagram form, the operation of the apparatus of FIGS. 2 to 4, FIG. 6 schematically illustrates the manner in which a correction factor is generated.

DESCRIPTION OF PREFERRED EMBODIMENT

Figure 5:
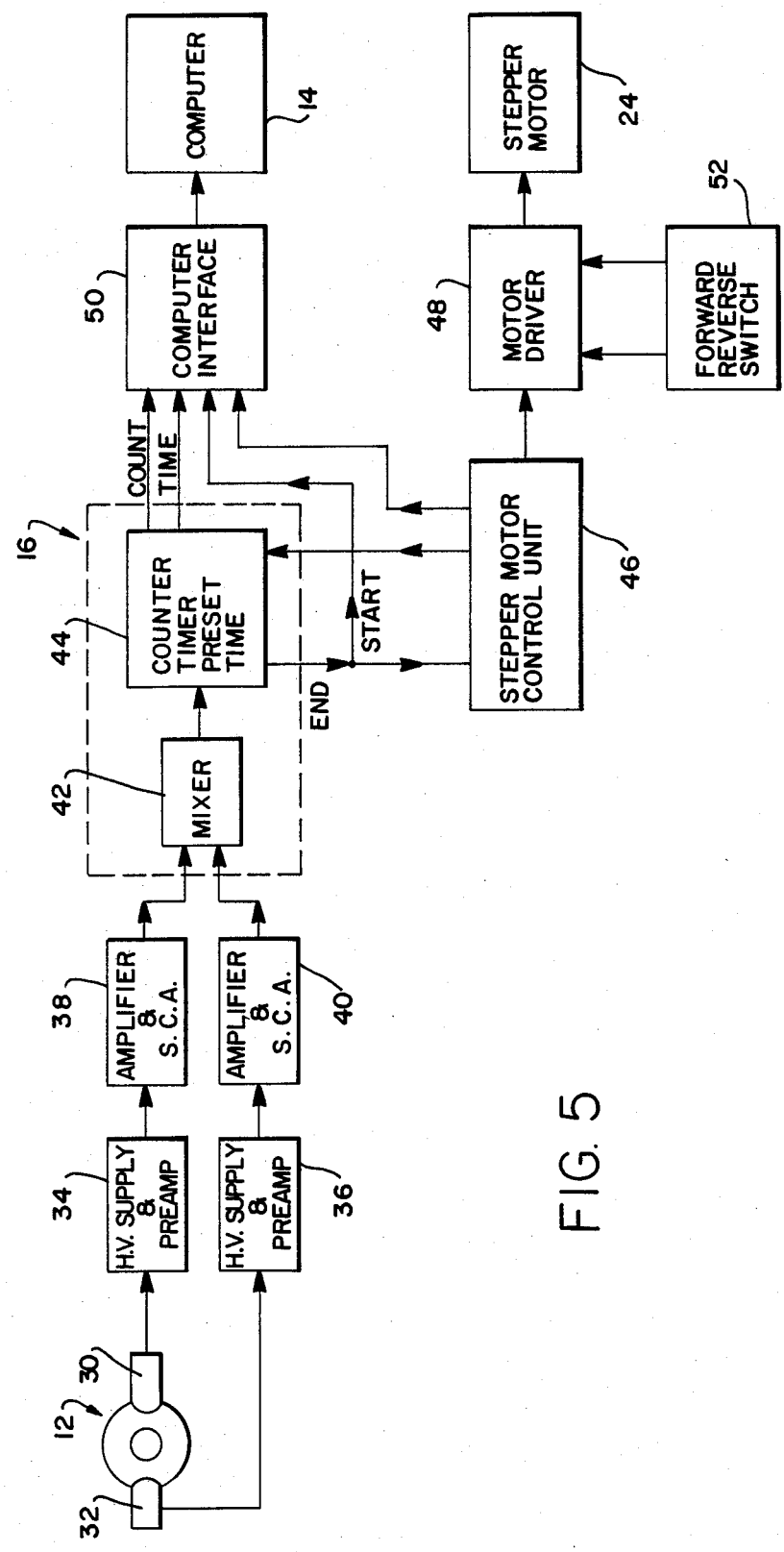

The histogram shown in FIG. 1 was derived by slicing segments approximately 1 cm thick from a borehole core with a 2 mm wide diamond saw and assaying each segment to determine the $U_3O_8$ content. The continuous curve was derived before the assaying process by radiometrically scanning the core with a suitable detector in steps of 1 cm and for each step deriving a radiometric count over a 10 second interval.

The core section of interest is approximately 40 cm long and a strong correlation exists between the continuous curve and the histogram. The continuous curve is however inaccurate in that the radioactive count taken for each segment is influenced by contributions from adjacent core segments.

The apparatus shown in FIGS. 2 to 5 is designed to log the radioactive content of a borehole core while taking into account radioactive emission from notional core segments on either side of the particular notional segment which is under direct measurement. The apparatus includes a core carriage 10, a detector 12, a computer 14, and control circuitry generally indicated by the reference numeral 16 in FIG. 5.

The core carriage 10 includes a stainless steel semi-cylindrical core receiving trough 18 which is mounted on guide and support rollers 20, and a pinion 22 which is driven by a stepper motor 24, see FIG. 5, which is engaged with a rack cut into the base of the trough 18. The pitch of the rack determines the resolution of movement and in this example is of the order of 1 mm.

The detector 12 includes an annular thallium activated sodium iodide scintillation crystal 26 which is mounted in lead shielding 28 and which is flanked by two photomultiplier tubes 30 and 32 respectively.

As shown in FIG. 5 the photomultiplier tubes are respectively connected to high voltage supplies and pre-amplifiers 34 and 36 and then to amplifiers and single channel analysers 38 and 40. The outputs of the analysers are applied to a mixer 42 which is connected to a counter/timer 44. The device 44 is connected to a stepper motor control unit 46 which controls a motor driver 48. The device 44 is also connected to the computer 14 via an interface unit 50. The driver 48 has a switch 52 for selecting the direction of movement of the motor.

A core 54 which is to be logged is placed in the trough 18 with the trough removed from the interior of the annular detector 12. The semi-cylindrical trough has the advantage that broken sections of core may be easily assembled and positioned in the trough.

The stepping motor 24 is controlled by means of the circuitry 16. This circuit permits the trough to be moved in steps of from 10 mm to 99 mm through a total distance of up to 1.5 m. The stepping time may also be varied and the trough may be held stationary relatively to the detector 12 for intervals of from 1 to 999 seconds.

As the trough 18 is stepped through the detector radiation from the core 54 is detected by the crystal 26. High voltage for the photomultipliers 30 and 32 is supplied via the units 34 and 36 respectively which also amplify the pulses produced by the photomultipliers and then feed the amplified signals to the single channel analysers 38 and 40.

The outputs of the analysers are fed to the mixer 42 and then to counter/timer 44 which effectively adds the signals over a preset period determined by the counter/timer 44. At the end of the preset time an output signal is applied to the computer interface 50 and the count is transferred via the interface to a storage device in the computer 14. The computer also records the number of steps advanced which corresponds to the core slice or segment number for the particular segment. Thus for each segment the computer records the core step number which is equivalent to the identity of the segment, the accumulated radioactive count, and the time interval over which the count is recorded.

The end of count signal is also applied to the stepper motor control unit 46. After a predetermined delay which is of the order of 1 second and which enables the transference of data to take place to the computer without interference from the stepper motor driver 48, the control unit 46 sends a predetermined number of pulses to the driver 48 which then drives the stepper motor 24 to advance the core by the predetermined notional segment thickness. The unit 46 has thumb wheel switches or the like which enable the pulses which are fed to the driver 48 to be varied and which thereby enable the notional segment thickness to be varied as well. Segment thickness is in this way, in this example, adjustable from 10 mm to 99 mm.

One second after the end of the step advanced the control unit 46 sends a start count signal to the counter timer 44 which then rests to zero. The count for the succeeding core segment is then initiated and the process described is repeated.

The sequence of stepping movement, count recordal, and storage of data is repeated until a predetermined number of steps, set in advance on the control unit 46, is reached. At this stage the sequence is automatically terminated. Micro switches may be mounted on the apparatus which are responsive to movement of the trough 18 to sense the limits of travel of the trough to terminate operation of the stepper motor should these limits be exceeded. The switch 52 permits movement of the stepper motor to take place in either direction and thus a core can be logged irrespective of its direction of movement relatively to the detector 12.

When the preset length of core has been stepped through the detector the radioactivity count and time data for each segment or core slice have been stored in the computer 14. This data may be retrieved and printed out to indicate the relationship between each segment and its radioactive count per second. Alternatively the data may be displayed graphically as indicated in the continuous curve of FIG. 1.

The count recorded for each segment is not due to that segment alone but is the sum of the count from that segment and the contributions from adjacent segments on each side of the segment in question. The distance over which the contribution from another segment is meaningful depends on the particular installation but the distance involved may be up to about 10 cm on each side of the segment in question.

Figure 6:
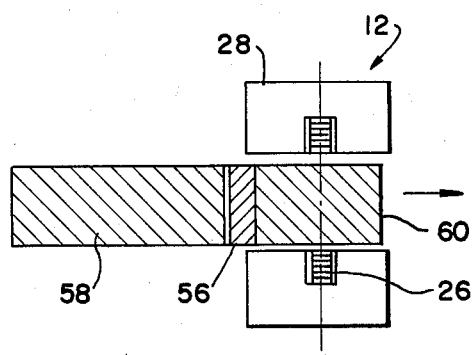
Figure 7:
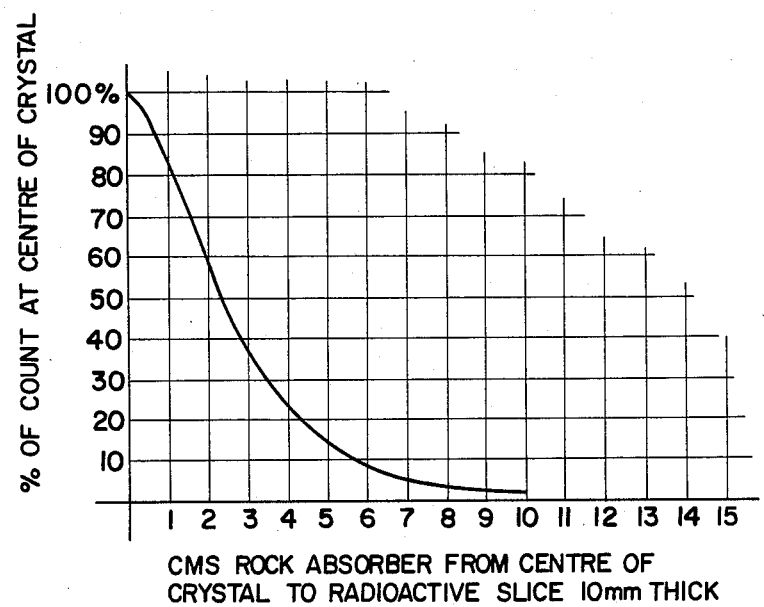
FIG. 7 illustrates a correction curve derived from the generation of the correction factor referred to, and FIG. 8 is a deconvoluted histogram derived from the continuous curve of FIG. 1 of corrected radioactive count for a plurality of core segments in a short section of core.

In accordance with a preferred feature of the invention a correction factor or curve is generated in advance which enables the contributions from adjacent segments to be compensated for. FIG. 6 illustrates the manner in which this is achieved. A high grade core segment 56 is located between barren lengths of core 58 and 60 and then passed through the detector 12. FIG. 7 illustrates a calibration curve produced from a count of radioactivity made by means of the detector 12 in respect of the segment 56. Generally speaking the curve is symmetrical on either side of a reference plane which passes through the centre of the crystal 26. In this particular example the segment 56 is 10 mm thick and it can be seen from FIG. 7 that the count recorded by the detector 12 is reduced to about 2% of the maximum when the segment is approximately 10 cm from the reference plane.

Figure 8:
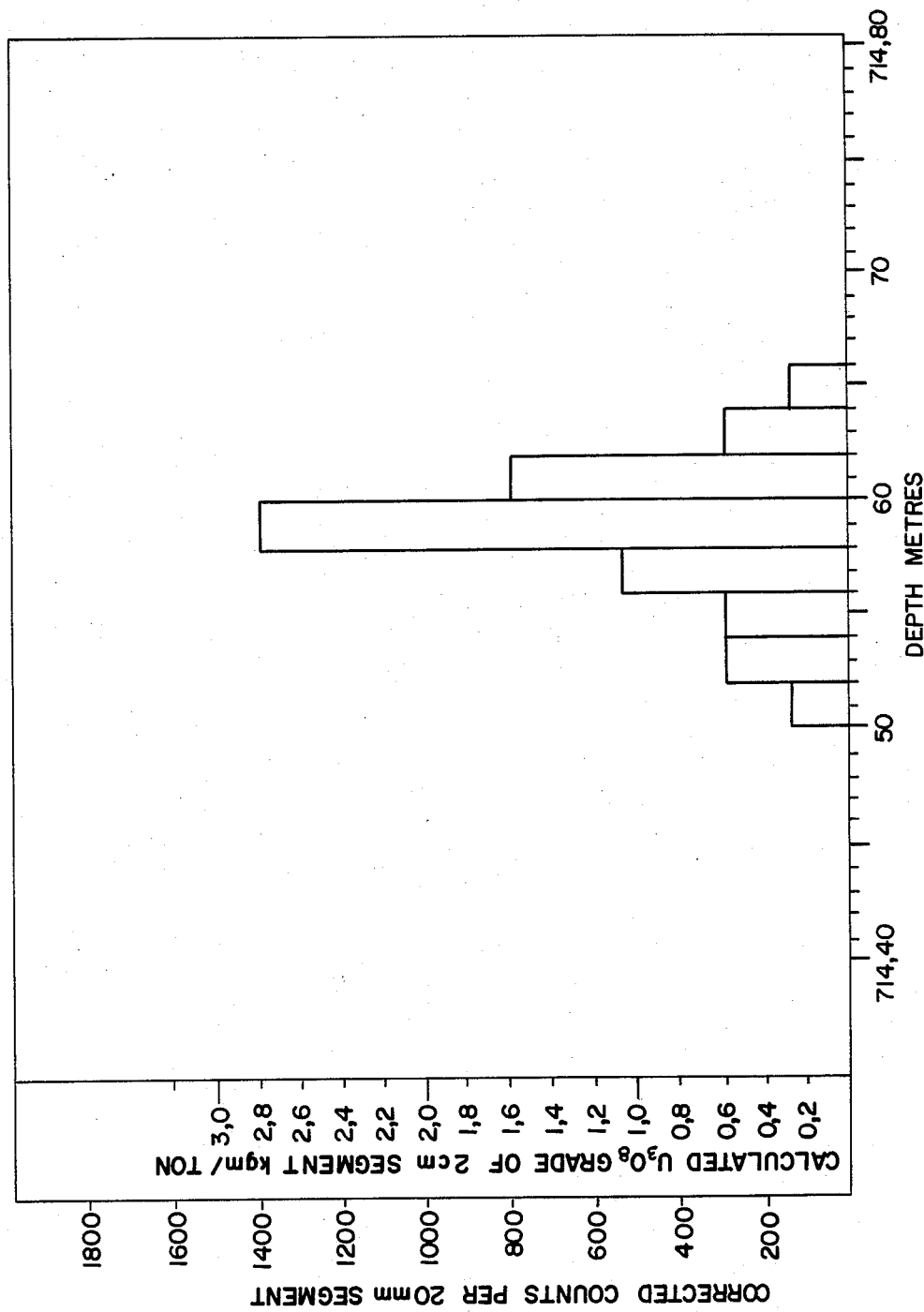

Calibration data corresponding to the curve shown in FIG. 7 is stored in the computer 14 and the summed count curve stored in the computer i.e. the continuous curve shown in FIG. 1 may then be deconvoluted using an iterative approximation process wherein the calculated resultant summed data points are repeatedly compared with the actual measured data point to determine the effective net contribution of each segment. In this way the actual or compensated count of each core segment is arrived at and a histogram of the actual count for each segment may be generated as shown in FIG. 8.

The invention has been described with particular reference to the generation of grade distribution curves for radioactive material. Clearly the principles of the invention are equally applicable to the evaluation of cores containing other material which emits radiation either naturally or as the result of a stimulation process.

We claim:

1. A method of logging a grade distribution of a borehole core which includes the steps of notionally dividing the core into a plurality of contiguous segments, obtaining a measure of a characteristic of each segment, using a correction factor, derived from measurements taken for a segment of known characteristics positioned in an otherwise barren core, to correct the measure for each segment to compensate for contributions to the measure due at least to adjacent segments, and recording the corrected measure for each segment.

2. A method according to claim 1 which includes the steps of causing relative stepped movement of the core and suitable measuring apparatus, each step of movement corresponding to the thickness of one segment, maintaining the core stationary relatively to the apparatus for a predetermined measuring period, making a measure of the characteristic of a predetermined segment, recording the measurement of the characteristic, and repeating the process as to obtain a measurement of the characteristic for each of the segments in succession.

* * * * *